Figures 1, 2:
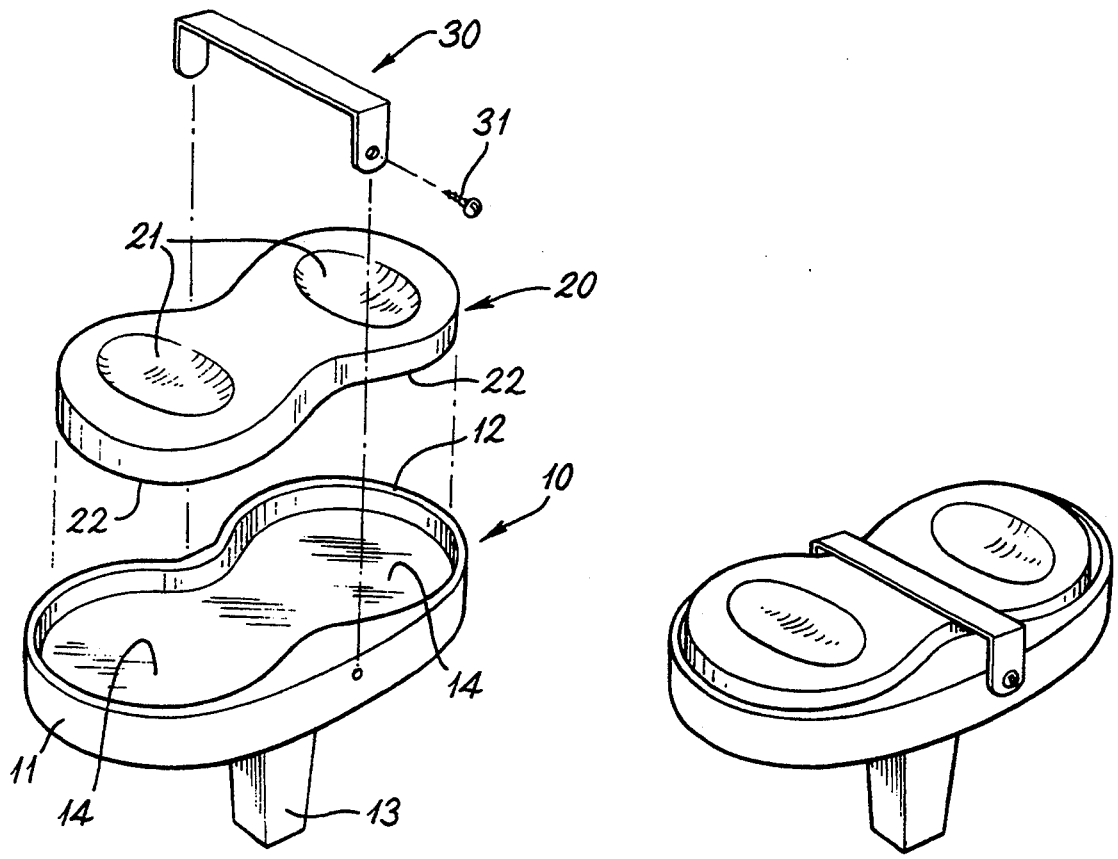

United States Patent
Goodfellow et al.

[11] Patent Number: 5,358,531
[45] Date of Patent: Oct. 25, 1994

[54] PROSTHETIC KNEE JOINT DEVICES

[75] Inventors: John W. Goodfellow, Woodeaton; John J. O'Connor, Headington, both of England

[73] Assignee: British Technology Group Limited, London, England

[21] Appl. No.: 104,930

[22] Filed: Aug. 12, 1993

Related U.S. Application Data

[63] Continuation of Ser. No. 842,336, Mar. 23, 1992, abandoned.

[30] Foreign Application Priority Data

Jun. 12, 1990 [GB] United Kingdom ............... 9103025

[51] Int. Cl.⁵ .............................................. A61F 2/30
[52] U.S. Cl. ................................................. 623/20
[58] Field of Search .................... 623/16, 17, 18, 19, 623/20, 21, 22, 23

[56] References Cited

U.S. PATENT DOCUMENTS

| | | | |
|---|---|---|---|
| 4,016,606 | 4/1977 | Murray et al. | |
| 4,030,143 | 6/1977 | Elloy et al. | 623/19 |
| 4,085,466 | 4/1978 | Goodfellow | |
| 4,193,139 | 3/1980 | Walker | 623/21 |
| 4,216,549 | 8/1980 | Hillberry et al. | 623/20 |
| 4,257,129 | 3/1981 | Volz | 623/18 |
| 4,634,444 | 1/1987 | Noiles | 623/18 |
| 4,728,332 | 3/1988 | Albrektsson | |
| 4,795,468 | 1/1989 | Hodorek et al. | 623/20 |
| 4,944,757 | 7/1990 | Martinez et al. | 223/20 |

FOREIGN PATENT DOCUMENTS

| | | |
|---|---|---|
| 0183670 | 6/1986 | European Pat. Off. |
| 2631351 | 2/1977 | Fed. Rep. of Germany |
| WO8503425 | 9/1985 | PCT Int'l Appl. |
| 1534263 | 11/1975 | United Kingdom |
| 2215610A | 2/1989 | United Kingdom |
| 1567007 | 5/1990 | United Kingdom |
| 2245175A | 1/1991 | United Kingdom |
| 2247407A | 9/1991 | United Kingdom |

*Primary Examiner*—David Isabella
*Attorney, Agent, or Firm*—Cushman, Darby & Cushman

[57] ABSTRACT

In or for a prosthetic knee joint device involving a femoral component having a convexly curved articulation surface a tibial component having a relatively flat articulation surface, and a meniscal component having two articulation surfaces in back-to-back disposition and respectively substantially complementary to, and for mutual engagement with, the femoral and tibial component articulation surfaces: an assembly of tibial and meniscal components including member separably connectable with the tibial component at least partially to bridge the meniscal component to retain their mutual articulatory engagement.

7 Claims, 1 Drawing Sheet

PROSTHETIC KNEE JOINT DEVICES

This is a continuation of application Ser. No. 07/842,336, filed on Mar. 23, 1992, which was abandoned upon the filing hereof.

This invention concerns prosthetic knee joint devices and more particularly such devices of the general kind described in Patent Specification GB 1534263.

Devices of this last kind can be defined as involving a femoral component having a convexly curved articulation surface, a tibial component having a relatively flattened articulation surface, and a meniscal component having two articulation surfaces in back-to-back disposition and respectively substantially complementary to, and for mutual engagement with, the femoral and tibial component articulation surfaces. These devices can employ components of unicompartmental, bicompartmental or, in the case of the femoral component, tricompartmental form, or components in a combination of such forms.

It is a feature of such a device that it can allow freedom of movement under the control of the related soft tissues in a natural manner and, at the same time, congruity between the engaged articulation surfaces. It is appropriate of course that movement should not lead to dislocation of the meniscal component but, given suitable design and application of the components, the component is normally retained in the desired manner between the associated components.

Even so, some forms of the device in current usage provide a mechanical coupling between the meniscal and tibial components with a view to ensuring the avoidance of dislocation while, at the same time, affording the desired mobility for the meniscal component. However, it is questionable whether this result can in fact be achieved fully satisfactorily by the couplings which have been proposed.

The couplings in question have commonly been of a tracked form involving a projection extending from one of the components into a recess in the other component. An immediate difficulty is that the freedom for movement is constrained and, in practice, congruity of articulation surface is degraded in compensation, but with consequent increase In contact stresses and component wear. There may also be a difficulty during surgery in locating the meniscal component between the femoral and tibial components and, at the same time, engaging the coupling without these last components being unduly spaced apart. This can lead to an incidence of undesirable laxity.

An object of the invention is to reduce the difficulties of this situation and, to this end, it is proposed that a device of the kind defined above should comprise an assembly of tibial and meniscal components formed for mutual articulatory engagement and including means separably connectable with the tibial component at least partially to bridge the associated meniscal component to retain their engagement.

As so far developed the invention is preferably applied to an assembly in which the meniscal and tibial components are each of one-piece bicompartmental construction having a pair of mutually spaced end portions respectively defining individual condylar articulation surfaces, such end portions being joined by way of a necked portion, and the separably connectable means including an elongate member at least partially to bridge the meniscal component necked portion.

Conveniently in this form of the invention, the elongate member passes over the necked portion of the meniscal component to allow the desired mobility for the latter. The convenience of this arrangement is that the necked portions of the components are located in the intercondylar space and the elongate member can pass wholly over the meniscal component without impact on related articulation capabilities.

An alternative possibility is that the member can pass through, or into, the meniscal component. While this possibility is less convenient for bicompartmental components in that the meniscal component is a less simple structure, it offers the benefit of application to unicompartmental components.

Figure 3:
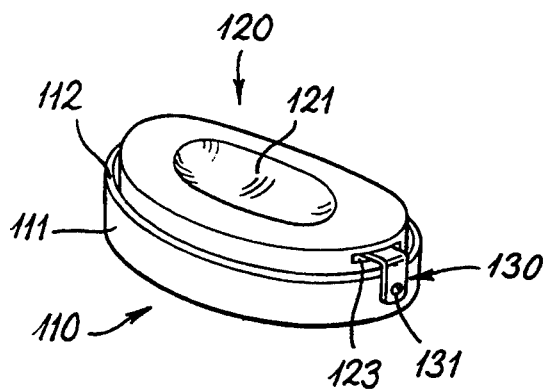

In any event, the invention is clarified by way of example with reference to the accompanying drawings in which FIGS. 1 and 2 respectively schematically illustrate in exploded and connected forms a presently preferred bicompartmental embodiment of an assembly according to the invention; and FIG. 3 similarly illustrates in connected form a unicompartmental embodiment.

The assembly of FIGS. 1 and 2 comprises a bicompartmental tibial component 10 of one-piece construction including a main plate-like body 11 having a peripheral rim 12 upstanding from one major surface and at least one stem or other element 13 projecting from the other such surface. As seen from its major surfaces, the main body has two similar end portions joined by way of a necked portion. The one major surface is planar with the end portions thereof respectively defining individual condylar articulation surfaces 14. The other major surface and its projecting element can be formed in any manner appropriate for securement to bone.

The assembly of FIGS. 1 and 2 also comprises a bicompartmental meniscal component 20 of necked plate-like body shape similar to that of the tibial component. However, the body in this case is of smaller transverse dimensions over its major surfaces, and has one such surface 22 planar, whereby it can seat on the one surface of the tibial component and articulate, within the limits of the rim of the latter, by translation and rotation. Also, the meniscal component body thickness is greater than the height of the tibial component rim to extend above the latter when seated therein. The other major surface of the meniscal component has respective concave articulation surfaces 21 formed in its end portions for engagement with an associated femoral component indicated in broken outline at 40.

Lastly in FIGS. 1 and 2, an elongate member 30 is provided. This member is of strip or other form having downwardly turned end portions and being dimensioned overall to bridge over the meniscal component, when this is seated in the tibial component, and engage its turned end portions with the tibial component. The member is secured in place by a screw 31 passed through one of the turned end portions into the tibial component.

It is to be noted that although the meniscal component will normally be located after the associated tibial and femoral components have been secured, and that the meniscal component must therefore pass over the tibial component rim, undue separation of the associated components is not necessary for this last purpose. The meniscal component can approach the site, with the leg fully flexed at the knee, from the front with its leading edge inclined downwardly within the upper tray-like formation of the tibial component, and then slid across this formation with a progressive downward rotation at its trailing edge to pass below and around the femoral component and fully seat in place. Thereafter the member 30 is conveniently located and secured from the front to act against meniscal component dislocation.

More particularly, it is to be noted that this securement against dislocation does not constrain the freedom for movement between the components in such a way as to require compensation by degraded congruity in articulatory engagement.

The assembly of FIG. 3 is similar to one end portion of that of FIGS. 1 and 2, and employs the same reference numerals for corresponding parts and features, but with the addition of a one hundred digit for purposes of distinction. A clear difference in the unicompartmental form of FIG. 3 is that the member 130 passes into a cavity 123 in, rather than over, the meniscal component 120.

While the invention has been described with more particular reference to the illustrated embodiments, it will be appreciated that other variations are possible. For example, it has been indicated that the separably connectable means need only partially bridge the meniscal component and this can entail variation in the extent to which the relevant member passes over or through the meniscal component. Also it will be evident that it is not necessary to have a rim wholly around the tibial component: the provision of short lengths of rim, or posts, at the front and rear of each condylar area can suffice to contain the meniscal movement relative to the tibial component within the appropriate controlled range.

We claim:

1. A prosthetic bone joint device comprising:
   a first component having a convexly curved articulation surface;
   a second component having a relatively flat articulation surface;
   a third component disposed between and engaging said first and second components for movement relative to each of said first and second components, said third component having two articulation surfaces in mutual back-to-back disposition, said two articulation surfaces being respectively complementary shaped to, but differently sized from, so as to allow mutual, rotational and translational engagement with, said convexly curved and said relatively flat articulation surfaces in the assembled device; and
   a member separably connected with said second component to project therefrom and at least partially bridge said third component to limit said relative movement and maintain said mutual engagement.

2. A device according to claim 1 wherein said member extends over a topmost surface said third component.

3. A device according to claim 1 wherein said third component is formed to include a cavity, and said member projects into said cavity 4. A device according to claim 1, 2 or 3 wherein said relatively flat articulation surface is planar and bounded by an upstanding rim formation.

5. A prosthetic knee joint device comprising:
   a meniscal component;
   a tibial component;
   said meniscal and tibial components each being of a bicompartmental form having a pair of mutually spaced end portions defining respective condylar articulation surfaces, with the end portions of each pair being interconnected by a respective reduced sized necked portion;
   said meniscal component end portions each having a concavely dished condylar articulation surface and a relatively flat condylar articulation surface in mutual back-to-back disposition;
   said tibial component condylar articulation surfaces respectively being of complementary shape to, but larger in size than, so as to allow rotational and translational engagement with, the relatively flat condylar articulation surfaces of said meniscal component for relative rotational and translational movement therebetween; and
   a member separably connected to said tibial component necked portion to project therefrom and at least partially extend over said meniscal component necked portion to retain said mutual engagement and limit said relative movement.

6. A device according to claim 5 wherein said relatively flat condylar articulation surfaces are each planar.

7. A device according to claim 5 or 6 wherein said tibial component has an upstanding rim formation bounding each said relatively flat condylar articulation surface.

* * * * *